US00PP16679P2

(12) United States Plant Patent
Boeder

(10) Patent No.: US PP16,679 P2
(45) Date of Patent: Jun. 20, 2006

(54) ***CHRYSANTHEMUM* PLANT NAMED 'DORA'**

(50) Latin Name: *Chrysanthemum morifolium*
Varietal Denomination: Dora

(75) Inventor: Mark Roland Boeder, The Hague (NL)

(73) Assignee: Chrysanthemum Breeders Association N.V. (NL)

( * ) Notice: Subject to any disclaimer, the term of this patent is extended or adjusted under 35 U.S.C. 154(b) by 75 days.

(21) Appl. No.: 11/020,165

(22) Filed: Dec. 27, 2004

(51) Int. Cl.
*A01H 5/00* (2006.01)

(52) U.S. Cl. ..... Plt./298
(58) Field of Classification Search ..... Plt./298
See application file for complete search history.

*Primary Examiner*—Anne Marie Grunberg
*Assistant Examiner*—Annette H Para
(74) *Attorney, Agent, or Firm*—Steptoe & Johnson LLP

(57) ABSTRACT

A *chrysanthemum* plant named 'Dora' characterized by its small sized blooms with red ray florets and prolific branching; natural season flower date October 18–25; blooming for a period of 4 weeks.

3 Drawing Sheets

BACKGROUND OF THE INVENTION

'Dora' is a product of a breeding and selection program for outdoor pot mums (garden mums) which had the objective of creating new *chrysanthemum* cultivars with a daisy type flower, a natural season flower date around October 18–25; blooming for a period of 4 weeks. The new plant of the present invention comprises a new and distinct cultivar of *chrysanthemum* plant 'Dora' is a seedling resulting from a crossing program, which was set up by a previous breeder, and which records are unknown to the inventor. The new and distinct cultivar was discovered and selected as a flowering plant by Mark Roland Boeder on a cultivated field in Rijsenhout, The Netherlands in 2001. The first act of asexual production of 'Dora' was accomplished when vegetative cuttings were taken from the initial selection in 2001 in a controlled environment in Rijsenhout, The Netherlands, and propagated further at this location. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
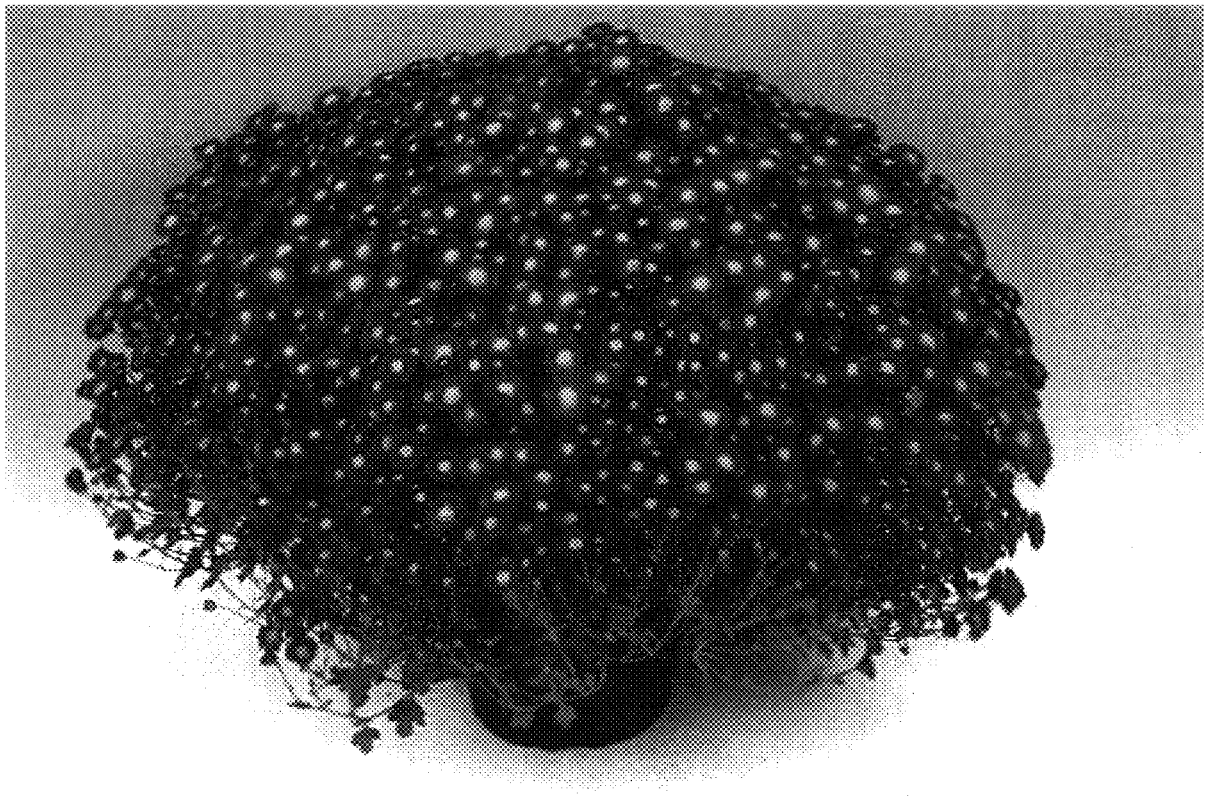
FIG. 1 shows a plant of the cultivar in full bloom.
Figure 2:
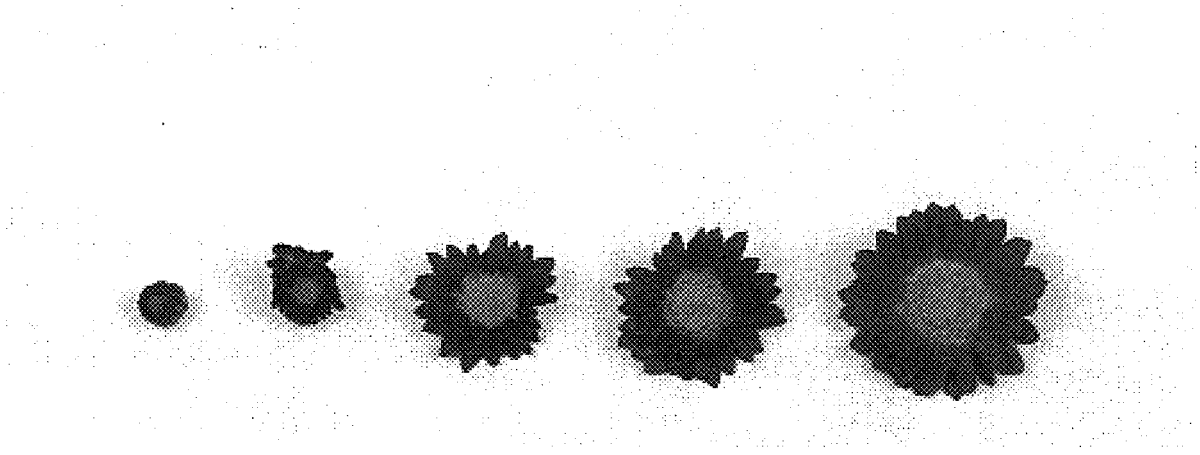
FIG. 2 shows the various stages of bloom of the new cultivar.
Figure 3:
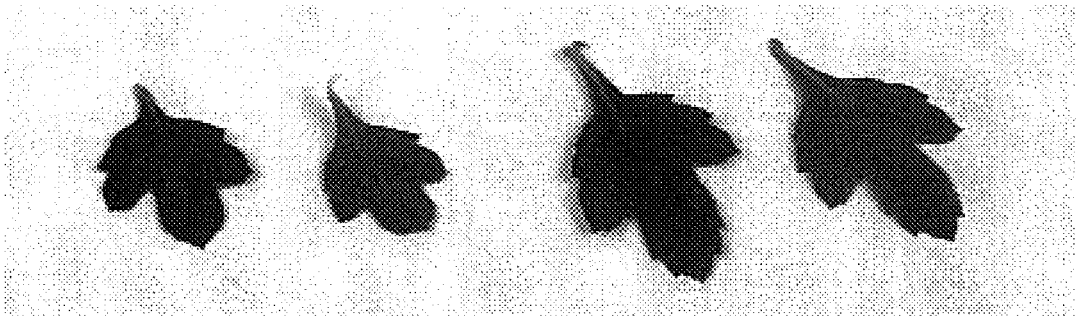
FIG. 3 shows the foliage of the new cultivar.

This new variety of *chrysanthemum* is of the botanical classification *Chrysanthemum morifolium* L. The observations and measurements were gathered from plants grown out door in Rijsenhout, The Netherlands under natural day length and temperature and planted week 24 in 2004. The natural blooming date of this crop was October 18–25 (week 43). The average height of the plants was 40 cm. No growth retardants were used. No tests were done on disease or insect resistance or susceptibility. No tests were done on cold or drought tolerance. This new variety produces small sized blooms with red ray florets and a yellow center blooming for a period of 4 weeks.

From the cultivars known to inventor the most similar existing cultivar in comparison to 'Dora' are 'Plutores' (U.S. Plant Pat. No. 12,919) and 'Cecaesar' (U.S. Plant Pat. No. 15,402). When 'Plutores', 'Cecaesar' and 'Dora' are being compared the following differences are noticed: The differences of 'Plutores', 'Cecaesar' and 'Dora' are (1) Bloom type. The flowers of 'Plutores' and 'Cecasear' are decorative, while those of 'Dora' are of daisy type. (2) Flower size. The flowers of 'Dora' are smaller in size than those of 'Plutores' and 'Cecaesar' (3) Color ray-florets. The red color of the ray-florets is differently shaded in the three varieties 'Dora', 'Plutores' and 'Cecaesar'.

The following is a description of the plant and characteristics that distinguish 'Dora' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

Botanical Description or *chrysanthemum* plant 'DORA'

| | |
|---|---|
| Bud | |
| Size | Small; cross-section 0.3 cm, height 0.2 cm |
| Outside Color | Greyed-purple 187B |
| Involucral bracts | 2 rows, length 7 mm, width 3 mm |
| Involucral bracts among disc-florets | Not present |
| Involucral bracts color | Green 139C |
| Bloom | |
| Type | Daisy |
| Height | 1 cm |
| Size | Small |
| Fully Expanded | 3 cm |
| Peduncle length | 3.5–4 cm |
| Peduncle color | Yellow-green 144A to Green 138A |

TABLE 1-continued

| Botanical Description or *chrysanthemum* plant 'DORA' | |
|---|---|
| Number of blooms per branch | Approx. 5–7 blooms per branch |
| Performance on the plant | 4 weeks |
| Seeds | Produced in small quantities, ovate grey-brown 199A, 1½ mm in length. |
| Fragrance | Typical *chrysanthemum,* slightly |
| Color | |
| Center of the flower (disc-florets) | Immature Yellow-green 145A<br>Mature Yellow-orange 15A |
| Color of upper surface of the ray-florets | Greyed-red 178B |
| Color of the lower surface of the ray-florets | Greyed-orange 175D |
| Tonality from Distance | A garden mum with red flowers and a yellow disc |
| Discoloration to color | Greyed-red 178B |
| Ray florets | |
| Texture | Upper and under side smooth |
| Number | 70–80 |
| Cross-section | Flat |
| Longitudinal axis of majority | Straight |
| Length of corolla tube | 0.3 cm |
| Ray-floret margin | Entire |
| Ray-floret length | 1.3 cm |
| Ray-floret width | 0.3 cm |
| Ratio length/width | High |
| Shape of tip | Pointed |
| Disc florets | |
| Disc diameter | 1 cm |
| Distribution of disc florets | Numerous, clearly visible at all stages |
| Shape | Tubular |
| Receptacle shape | Conical raised |
| Reproductive Organs | |
| Stamen | Present in disc florets only |
| Stamen color | Yellow-green 144A |
| Pollen | Present |
| Pollen color | Yellow 7A |
| Styles | Thin |
| Style color | Yellow 13A |
| Style Length | 3 mm |
| Stigma color | Yellow-green 144A |
| Stigma Width | 1 mm |
| Ovaries | Enclosed in calyx |
| Plant | |
| Form | Grown as a spray type potmum, outdoor mounded and round |
| Growth habit | Spherical shape |
| Growth rate | Medium vigor |
| Height | 40 cm |
| Width | 55 cm |
| Stem Color | Greyed-brown 199B |

TABLE 1-continued

| Botanical Description or *chrysanthemum* plant 'DORA' | |
|---|---|
| Stem Strength | Strong |
| Stem Brittleness | Not brittle |
| Stem Anthocyanin Coloration | Absent |
| Internode length | 1.5–3 cm |
| Length of lateral branch | From top to bottom 13 cm |
| Lateral branch color | Yellow-green 144B |
| Lateral branch, attachment | Medium strength |
| Branching (average number of lateral branches) | Prolific with 8–10 breaks after pinching |
| Natural season blooming date | October 18–25 |
| Foliage | |
| Leaf color | Upper side Green 137A<br>Lower side Green 138A |
| Color midvein | Upper side Green 138C<br>Lower side Green 139D |
| Size | Small; length 2–3.5 cm width 2–2.5 cm |
| Quantity (number per lateral branch) | 18–20 |
| Shape | Ovate |
| Texture upper side | Glabrous |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Truncate |
| Apex | Mucronulate |
| Petiole length | 0.5 cm |
| Petiole color | Green 138C |

TABLE 2

| Differences with the comparison varieties | | | |
|---|---|---|---|
| | 'Dora' | 'Plutores' | 'Cecaesar' |
| Bloom type | Daisy | Decorative | Decorative |
| Flower size | 3 cm | 4.5 cm | 5.5 cm |
| Color upper side ray-florets | Greyed-red 178B | Red 46A | Greyed-red 178D at tip and Yellow 7C at base |

I claim:

1. A new and distinct variety of *chrysanthemum* plant as described and illustrated.

* * * * *